United States Patent [19]

Mulligan et al.

[11] Patent Number: 5,037,758
[45] Date of Patent: Aug. 6, 1991

[54] ENHANCED PRODUCTION OF BIOSURFACTANT THROUGH THE USE OF A MUTATED B SUBTILIS STRAIN

[75] Inventors: Catherine N. Mulligan, Lachine; Terry Y-K Chow, Montreal, both of Canada

[73] Assignee: Her Majesty the Queen in right of Canada, as represented by The National Research Council of Canada, Ottowa, Canada

[21] Appl. No.: 296,215

[22] Filed: Jan. 11, 1989

[51] Int. Cl.$^5$ ............................................. C12N 1/20
[52] U.S. Cl. ............................. 435/252.5; 435/172.1; 435/839; 435/71.2
[58] Field of Search ............. 435/172.1, 252.31, 252.5, 435/839

[56] References Cited

U.S. PATENT DOCUMENTS 3,687,926 8/1972 Arima et al. .................. 435/839

FOREIGN PATENT DOCUMENTS 235461 11/1984 Fed. Rep. of Germany .
2172898 10/1986 United Kingdom .

OTHER PUBLICATIONS

Cooper et al., "Enhanced Production of Surfactin from *Bacillus subtilis* By Continuous Product Removable and Metal Cation Additions," *Applied and Environmental Microbiology*, vol. 42 (3), pp. 408–412 (1981).

Guerra-Santos et al., "Dependence of *Pseudomonas aeruginosol* Continuous Culture Biosurfactant Production on Nutritional and Environmental Factors", *Applied Microbiology and Biotechnology*, vol. 24, pp. 443–448 (1986).

*Primary Examiner*—Douglas W. Robinson
*Assistant Examiner*—Marian C. Knode
*Attorney, Agent, or Firm*—Oblon, Spivak, McClelland, Maier & Neustadt

[57] ABSTRACT

A *B. subtilis* strain possessing an enhanced surfactin production potential. The strain is a mutant of *B. subtilis* ATCC 21332 and has at least one mutation between Arg4 and HisA1 sites of the genetic map of *B. subtilis* ATCC 21332. Also included in the present invention is *B. subtilis* strain having the identifying characteristics of ATCC 53813.

3 Claims, No Drawings

ENHANCED PRODUCTION OF BIOSURFACTANT THROUGH THE USE OF A MUTATED B SUBTILIS STRAIN

BACKGROUND OF THE INVENTION

Biosurfactants are substances that have received a considerable amount of attention because of the fact that they possess a wide variety of interesting properties. For example, they can be used as oil recovery agents, emulsifiers, antibiotics and antifungal agents. In fact, Arima et al. have demonstrated in 1968 *Biochem. Biophys. Res. Commun.* 31:488–494 that a biosurfactant such as surfactin could reduce the surface tension of water from 72 to 27 mN/m at a concentration as low as 0.005% and could also inhibit clot formation. Furthermore, Bernheimer and Avigad in 1970 *J. Gen. Microbiol.* 61:361–369 have shown that surfactin could efficiently lyse erythrocytes while Hosono and Suzuki in 1983, *J. Antibiot.* 36:679–683 have demonstrated that bacterial spheroplasts and protoplasts as well as cyclic 3',5'-monophosphate diesterase could also be inhibited by the action of surfactin.

Biosurfactants are produced as metabolic products or membrane components. A considerable number of these compounds have been characterized and described by various authors such Cooper et al. (1986, *Microbiol. Sci.* 3:145–149), Cooper and Zajic (1980, *Adv. Appl. Microbiol.* 26:229–253), Margaritis et al. (1979, *Biotech. Bioeng.* 21:1151–1161), Rosenberg (1982, *CRC Crit. Rev. Biotech.* 1:109–132), Zajic and Steffens (1984, *CRC Crit. Rev. Biotech.* 1:87–107). These compounds are classified as lipopeptides, glycolipids, lipopolysaccharides, neutral lipids and fatty acids or phospholipids. They are surface-active due to their hydrophobic and hydrophilic regions. Since surfactants are used in many multiphase processes, they are very important industrially. Biosurfactants are potentially less toxic and more biodegradable than the synthetic compounds currently used. They can also be produced from a variety of substrates.

In particular, lipopeptides are a very interesting class of compounds. Some examples such as amphomycin (Bodanszky et al. 1973, *J. Am. Chem. Soc.* 95:2352–2357 and cyclosporin A (Dreyfuss et al., 1976, *Eur. J. Appl. Microbiol.* 3:125–133; Rüegger et al. 1976, *Helv. Chim. Acta* 59:1075–1092) are respectively known for their antibiotic and antifungal activities. They contain both a lipid portion and several amino acids.

*Bacillus subtilis* ATCC 21332 produces surfactin. Surfactin is a lipopeptide biosurfactant having as mentioned above quite interesting properties. Apart from being a very powerful biosurfactant, surfactin has the advantage of being easily isolated in pure form when produced by microorganisms such as *B. subtilis*. However, serious problems are associated with the industrial production of surfactin. Among these problems, the fact that the yields are very low is certainly the most important one.

Until now, the only methods which have been utilized to enhance production of surfactin by *B. subtilis* are strain selection or the manipulation of environmental or nutritional factor such as described in Cooper et al. in 1981, *Appl. Environ. Microbiol.* 42:408–412 and Guerra-Santos et al. in 1986 *Appl. Microbiol. Biotech.* 24:443–448. However, the methods that have been proposed so far are indirect methods having their limitations.

Therefore, the obtention of a *B. subtilis* strain able to produce large quantities of surfactin would be highly desirable.

SUMMARY OF THE INVENTION

In accordance with the present invention, there is provided a novel *Bacillus subtilis* strain whose genetic material has been modified through UV mutagenesis and which may be used for producing surfactin at levels which are higher than the levels encountered when wild type *Bacillus subtilis* is employed. The genetically modified strain of the present invention is a mutant of *Bacillus subtilis* ATCC 21332 having at least one mutation between Arg4 and HisA1 sites of the genetic map of *B. subtilis* ATCC 21332.

In fact, when biosurfactant production by the mutant strain of the present invention is compared to that of the parent strain, it is found that the mutant strain produces as much as 3 to 4 times more biosurfactant than the parent strain in equivalent growth conditions over the same period of time.

Particularly, a subject mutant strain obtained through U.V. radiation was deposited on Sept. 21, 1988 at the American Type Culture Collection, 12301 Parklawn Drive, Rockville, Md., 20852 and was given the ATCC accession number 53813.

The mode of obtention as well as the utility of the mutant strain of the present invention will be more readily illustrated by referring to the following description.

DETAILED DESCRIPTION OF THE INVENTION

The present invention relates to a novel bacterial strain of *Bacillus subtilis* obtained through genetic mutation by ultraviolet light of the *Bacillus subtilis* prototroph strain ATCC 21332. The obtention of this strain allows for higher yields in the production of surfactin, a lipopeptidic biosurfactant possessing exceptional surface activity.

Obtention and selection of the mutant microorganism

The purpose of the work that lead to the present invention was to increase the yield in surfactin secretion by *Bacillus subtilis* through genetic manipulations. Mutation has been chosen since any change in the regulatory system of biosurfactant synthesis and secretion would result in an altered level of production.

Thus, in order to obtain a mutant *B. subtilis* strain producing increased amounts of surfactin, *Bacillus subtilis* prototroph strain ATCC 21332 may be grown to logarithmic phase and then approximately 3000 cells are plated on nutrient agar plates. The plates are then UV radiated for 35 seconds with short wave in a Chromato-Vue Cabinet Model CC-60 (UVP, Inc.). This dosage of UV light had been previously determined to give a 10 to 20% survival rate in the colonies. The UV-radiated plates are then incubated at 37° C. in the dark until the colonies are visible.

In order to detect whether the obtained colonies produce enhanced amounts of biosurfactant, the *B. subtilis* mutants derived from UV mutagenesis are replica plated or individually spotted onto rich medium agar plates containing 5% sheep blood cells, 4% glucose, 0.1% nutrient broth, 0.1% yeast extract and mineral salts, as described by Cooper et al. in 1981 *Appl.*

*Environ. Microbiol.* 42:408-412. These plates are then screened for enhanced haemolytic activity by incubation at 37° C. and by evaluation of the haemolytic zone surrounding the colonies. It has been demonstrated by Mulligan et al. in 1984, *J. Ferm. Technol.* 62:311-314 that the degree of lysis of red blood cells is related to the level of surfactin production by *B. subtilis*.

The mutant that produces a significantly larger haemolytic zone around the colony than the other survived colonies in the parent strain is chosen. This mutant is not an auxotroph as it grew on minimal media.

Determination of the location of the mutation

The location of the mutation responsible for enhanced surfactant production is determined through protoplast fusion between the enhanced production mutant and BGSC strain 1A28 (ArgC4, HisA1 and TrpC2). This fusion may be carried out according to the method by Akamatsu and Seguchi in 1987, *Mol. Gen. Genet.* 298:254-262. It was determined that either a single mutation or mutations clustered in a small region of DNA that acted as a unit may be responsible for the enhanced biosurfactant production of *B. subtilis*. The genetic mapping of the ATCC 53813 mutant with a standard marker strain, *B. subtilis* IA28 demonstrated that the mutation was located between ArgC4 and HisA1 on the genetic map. Numerous mutations between these two sites could also lead to an increased production of surfactant.

Evaluation of the surfactin production of the mutant B. subtilis strain

From a sheep blood agar plate, the *B. subtilis* mutant strain is inoculated into a 500 ml flask containing 100 ml of 4% glucose and mineral salts medium as described by Cooper et al. in 1981, *Appl. Environ. Microbiol.* 42:408-412 supplemented with $3.2 \times 10^{-4}$M FeSO$_4$. After 3 days of growth, 10 ml of the culture is transferred to another similar flask. After 6 hours of growth, 100 ml of this media may be used as an inoculum for a 3.7 l CHEMAP fermentor.

The fermentor is operated under the following conditions: a 2.0 l working volume, a temperature of 37° C., a 5.0 l/min aeration rate and pH control at 6.7. The surfactin concentrated in the foam is removed continuously into a flask on the air exhaust line as described by Cooper et al., in 1981, *Appl. Environ. Microbiol.* 42:408-412.

Optical density is to be monitored at 600 nm throughout growth. Samples with optical densities above 1.0 may be diluted to obtain a reading in the appropriate range. The readings are then multiplied by the dilution factor. Surface tension of the medium may be measured using a Fisher Surface Tensiomat Model 21 which employs the du Noüy method.

Surfactin may then be isolated by adding concentrated HCl to the broth after cell removal by centrifugation as described by Cooper et al. in 1981, *Appl. Environ. Microbiol.* 42:408-412. The precipitated crude surfactin is then extracted 3 times with equal volumes of dichloromethane. This is followed by the removal of the solvent through evaporation under pressure. The surfactin may be further purified by redissolving in water (pH adjusted to 8.0 by the addition of NaOH), filtration through Whatman no. 1 paper, and re-extracting 3 times with the same solvent.

The amount of biosurfactant in the medium is determined by amino acid analysis. In order to do so, a 10 ul aliquot is dried and acid hydrolysed for 2.5 hours at 150° C. in a Waters PICO-TAG Amino Acid Analysis System. The residue is then redissolved in 200 ul of sodium buffer and injected on a Beckman System 6300 High Performance Analyser equipped with a Beckman Model 7000 Data Station. Analyses are performed according to the general procedures described by Spackman et al. in 1958, *Anal. Chem.* 30:1190-1206. The ratio of aspartic acid, glutamic acid, valine and leucine is found to be approximately 1:1:1:4 for the compounds produced by each strain. This ratio is similar to the amino acid composition of surfactin shown by Kakinuma et al. in 1969 *Agric. Biol Chem.* 33:1669-1671.

Further confirmation of the structure of the biosurfactants may be obtained by mass spectrometry. Based on the surfactin molecular formula ($C_{53}H_{93}N_7O_{13}$), the protonated molecular weight is 1036.6909. The spectra of the compounds produced by the parent strain shows similar fragmentation patterns with respective $M^+$ of 1036 and 1037. The mass spectra were obtained on a VG Analytical ZAB-SE double focussing mass spectrometer. The accelerating voltage was 10 kV and the fast xenon atom beam was operated with an emission current of 1 mA at 8 kV. Mass spectra were recorded with the data acquisition and calibration was performed with CsI.

Surfactant production was compared to the production of surfactin by *Bacillus subtilis* ATCC 21332 under similar growth conditions. Results shown in Table 1 demonstrate that the mutated strain of the present invention can produce at least 3 to 4 times more biosurfactant than the parent strain over the same time period.

TABLE 1

| | | |
|---|---|---|
| Comparison of the growth and the amounts of biosurfactant produced by *B. subtilis* and the mutant strain of the present invention | | |
| Strain | Growth after 40 hours (Optical density at 600 nm) | Amount of surfactin produced (mg) |
| ATCC 21332 | 8.2 | 328 |
| ATCC 53813 | 8.3 | 1124 |

We claim:

1. A biologically pure culture of a *Bacillus subtilis* strain possessing an enhanced surfactant production potential and having at least one mutation between the Arg4 and HisA1 sites of the genetic map of *B. subtilis* ATCC 21332.

2. The biologically pure culture of *B. subtilis* strain of claim 1, wherein the mutation is obtained through ultraviolet light exposure.

3. A biologically pure culture of *Bacillus subtilis* strain ATCC 53813.

* * * * *

UNITED STATES PATENT AND TRADEMARK OFFICE
CERTIFICATE OF CORRECTION

PATENT NO. : 5,037,758

DATED : AUGUST 6, 1991

INVENTOR(S) : CATHERINE N. MULLIGAN ET AL

It is certified that error appears in the above-identified patent and that said Letters Patent is hereby corrected as shown below:

On the title page, Item [75]: Inventors: "Catherine N. Mulligan, Lachine, and Terry Y-K Chow, Montreal"

Should read --Catherine N. Mulligan, Lachine, Terry Y-K Chow, Montreal, and Bernard Gibbs, Montreal--.

Signed and Sealed this

Eighth Day of March, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,037,758

DATED : AUGUST 6, 1991

INVENTOR(S) : CATHERINE N. MULLIGAN ET AL

It is certified that error appears in the above-identified patent and that said Letters Patent is hereby corrected as shown below:

On the title page, Item [75]: Inventors: "Catherine N. Mulligan, Lachine, and Terry Y-K Chow, Montreal"

Should read --Catherine N. Mulligan, Lachine, Terry Y-K Chow, Montreal, and Bernard Gibbs, Montreal--.

This request was erroneously issued this request was denied on February 4, 1994.

This request supersedes certificates of correction issued on March 8, 1994.

Signed and Sealed this

Twenty-sixth Day of April, 1994

Attest:

BRUCE LEHMAN

Attesting Officer

Commissioner of Patents and Trademarks